United States Patent [19]

Matsumoto

[11] 4,320,977

[45] Mar. 23, 1982

[54] METHOD FOR OPTICALLY ASSAYING LIQUID SAMPLES WITH POLYGANOL TRANSPARENT STIRRER

[75] Inventor: Shinichiro Matsumoto, Tokyo, Japan

[73] Assignee: Mitsubishi Chemical Industries, Limited, Tokyo, Japan

[21] Appl. No.: 152,161

[22] Filed: May 22, 1980

[30] Foreign Application Priority Data

Jun. 13, 1979 [JP] Japan .................................. 54/74253

[51] Int. Cl.³ ............................................ G01N 21/59
[52] U.S. Cl. ..................................... 356/427; 356/440
[58] Field of Search ............... 356/338, 427, 246, 440, 356/442; 424/12

[56] References Cited

U.S. PATENT DOCUMENTS 4,125,327 11/1978 Margolis .............................. 356/427

Primary Examiner—Vincent P. McGraw
Attorney, Agent, or Firm—Oblon, Fisher, Spivak, McClelland & Maier

[57] ABSTRACT

There is disclosed a method for optically assaying a liquid sample which comprises placing the liquid sample in a cell for optical measurement equipped with a stirrer having a thick polygonal prism portion made of a transparent material, said polygonal prism portion of the stirrer being positioned within the path of light used for the measurement, and measuring an optical property of the sample with stirring by rotation of the stirrer.

13 Claims, 4 Drawing Figures

METHOD FOR OPTICALLY ASSAYING LIQUID SAMPLES WITH POLYGANOL TRANSPARENT STIRRER

BACKGROUND OF THE INVENTION

1. Field of the Invention

This invention relates to a method for optically assaying liquid samples. More particularly, it relates to a method for assaying extremely small amounts of samples for their optical properties with high precision.

2. Description of the Prior Art

It is known that when a reaction is conducted in a cell for use in optical measurement the change in an optical property such as optical density of the sample with the progress of the reaction can be followed by an optical means to learn the progress of the reaction. This technique has been applied to various assay systems, for example, assay of an antigen or antibody by its antigen-antibody reaction with a sensitized latex, which system has recently been in the limelight. In a typical antigen-antibody reaction, a sensitized latex comprising insoluble carrier particles having an average diameter of not greater than 1.6 microns on which the appropriate antigen or antibody has been supported is placed in a cell for optical measurement and an antibody- and/or antigen-containing sample is added to cause the desired antigen-antibody reaction with stirring. The cell is irradiated with light of wavelengths in the range of 0.6 to 2.4μ and greater than the average diameter of the latex particles by a factor of at least 1.1 and preferably at least 1.5, and the change in an optical property of the latex, usually amount of transmitted light, is measured. In this way, the sample can be assayed usually by determining the velocity of change in absorbance or transmittance, the absorbance after a given period, or the time required to reach a given absorbance (see U.S. Pat. No. 4,118,192). In such assay of antigen-antibody reactions, it is necessary to agitate the liquid in the cell with adequate vigor in order to keep the content of the cell uniform and accelerate the reaction. A conventional stirrer occupies only a small part of the cell volume and is positioned out of the path of irradiated light. If such stirrer is positioned within the light path, it is usually removed out of the light path prior to the measurement so as to avoid incorrectness of the measurement due to absorption or scattering of light by the stirrer. However, such procedure is generally not favorable for assay of minute volume of samples.

Therefore, there is a continuing need for methods for assaying extremely small amounts of samples for their optical properties with high precision.

SUMMARY OF THE INVENTION

The present invention provides a method for optically assaying a liquid sample which comprises placing the liquid sample in a cell for optical measurement equipped with a stirrer having a thick polygonal prism portion made of a transparent material, said polygonal prism portion of the stirrer being positioned within the path of light used for the measurement, and measuring an optical property of the sample with stirring by rotation of the stirrer.

BRIEF DESCRIPTION OF THE DRAWINGS

In FIG. 2, the radius of curvature of the bottom is 2.5 R and the length of the prism portion (L) is 6.5 mm.

1 indicates an axis; 2, a cylindrical portion; 3, a prism portion; and 4, a round bottom.

Figure 4:
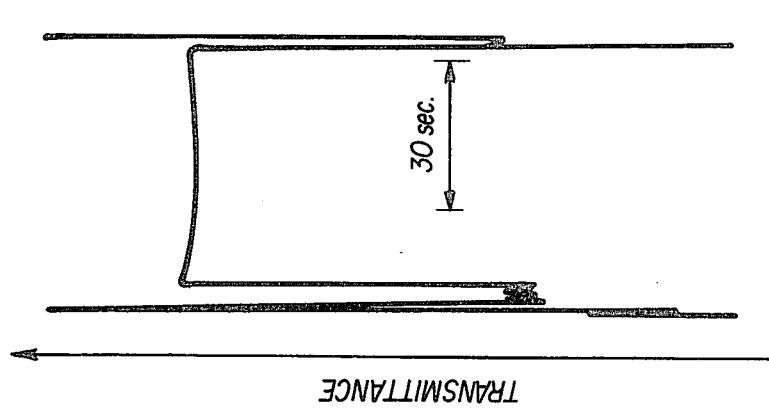
Figure 3:
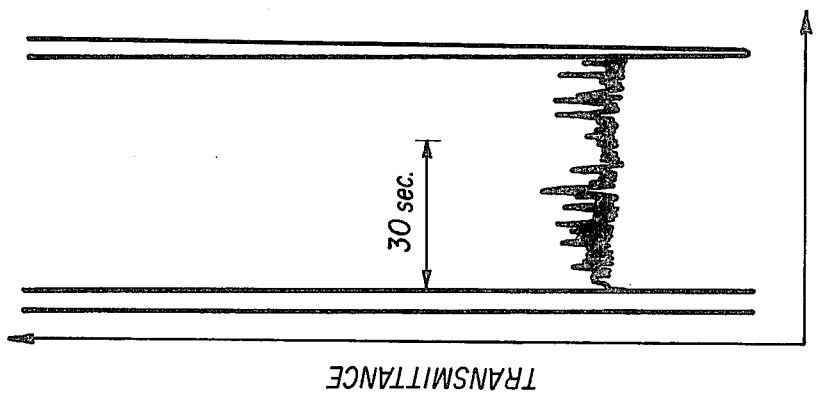

FIGS. 3 and 4 show typical charts of transmittance obtained by use of stirrers A and B, respectively, in Example 3.

DETAILED DESCRIPTION OF THE PREFERRED EMBODIMENTS

Further details of the invention will be found in the following description.

The measuring apparatus used in this invention is provided with a cell for optical measurement in which a liquid sample is held, a stirrer inserted in the cell, a light source for irradiating the cell with light for measurement and a receptor for measuring the light transmitted through the cell. The light source and the receptor employed may be the same as those employed in similar conventional optical measuring apparatus. Usually the cell may also be a conventional one which is generally used in optical measuring apparatus and has a cross-sectional shape of rectangular or square. On the contrary, the stirrer used in this invention is different from conventional stirrers in that at least a portion of the part of the former stirrer which is to be immersed in the liquid sample is made of a transparent material such as glass or a transparent synthetic resin, e.g., polyethylene, polystyrene, polymethyl methacrylate and the like and is formed in the shape of prism having a polygonal cross-section. A stirrer having a polygonal cross-section can exert a greater stirring effect than that of a circular cross-section. It is usually preferred that when the stirrer is inserted into the liquid the length of the polygonal prism portion of the stirrer should be equivalent to at least 30% of the depth of the liquid. The cross-section of the prism portion preferably has a rectangular or regular hexagonal shape in which the opposite sides are parallel to each other. Such cross-sectional shape is effective in minimizing the scattering of light from the stirrer. In view of stirring effect and light scattering, the most preferred cross-sectional shape of the stirrer is considered to be square.

While the stirrer has the same cross-sectional shape over the length of the part thereof which is to be immersed in a liquid, it is preferred that the portion of the stirrer adjacent to the liquid surface should be circular in cross-section or in the shape of a cylinder. When the portion of a stirrer adjacent to the liquid surface is in the shape of a polygonal prism and such stirrer is rotated at a high speed, air bubbles are entrapped in the liquid at its surface, which may result in an error in the measurement. On the other hand, with a stirrer having a cylindrical portion adjacent to the liquid surface, entrapment of air bubbles is significantly reduced even at a high rotation speed. Generally a stirrer having a cylindrical portion extending to at least 1 mm below the liquid surface, preferably to 1 to 5 mm below the liquid surface can avoid the hindrance attributable to entrapment of air bubbles.

Preferably the stirrer is as large as it can rotate in the cell. Generally a stirrer is selected so as to have a cross-sectional area equivalent to at least 25%, preferably at least 30% of the effective cross-sectional area of the cell. A stirrer having a larger cross-sectional area can fill the inner space of the cell with smaller volume of a liquid sample. With such stirrer, also the scattering and the absorption of light by the liquid sample are decreased since the light for measurement is passed through the liquid for a shorter distance. Thus, a thick stirrer permits precise measurement of liquid samples even if they absorb or scatter light in a large degree. When the minimum distance (gap) between the stirrer and the inside wall of the cell is from 0.5 to 2 mm in the rotating state of the stirrer, the above-mentioned advantages attained by use of a thick stirrer is compatible with free rotation of the stirrer.

In order to measure an optical property of the liquid in the cell in accordance with the method of the invention, a stirrer having a specifically shaped transparent portion as described above is inserted in the cell, said transparent, polygonal prism portion being positioned within the path of the light for measurement, and it is rotated as the cell is irradiated with light. The distance through the liquid which is passed by the light, i.e., the light-path length (cell thickness) and the proportion of the intensity of light scattered by the stirrer to that of the transmitted light vary periodically depending on rotation of the stirrer. For this reason, the optical property measured at each moment varies periodically even if the sample is absolutely unchanged. However, when the velocity of the stirrer is as high as from several hundred to several thousand revolutions per minute and the measuring apparatus is a conventional one, an average of the periodic variation is automatically measured so that there is no difficulty in the measurement. If the velocity of the stirrer is so low that the measurement is influenced by the periodic variation with rotation of the stirrer, the measurement of an optical property can be performed by integrating the measured values over a given length of time which is required for more than a few cycles of rotation. It is a matter of course that the stirrer be rotated at a considerably higher speed than the velocity of change in optical properties of the sample being measured so that the influence of rotation can be eliminated with no influence on the change in optical properties of the sample.

In accordance with the method of the invention, since the presence of a stirrer does not hinder the measurement, one can measure an optical property in the region of the cell where the liquid is directly stirred with a stirrer, with minimum influence of stirring on the measurement.

In addition, the effective light-path length is decreased and therefore it is possible to increase the absorbance or degree of scattering of a sample per unit light-path length. Accordingly, in the case of an antigen-antibody reaction in a sensitized latex, the sensitivity of the measurement can be improved by use of a latex having a higher concentration and/or containing larger latex particles.

While with a propeller or turbine-type agitator blade a shear stress is applied to the inside of the liquid as the blade is rotated, the stirrer in the shape of a polygonal prism used in practice of the invention does not create a significant shear stress with its rotation. Accordingly, in the case of an antigen-antibody reaction in a sensitized latex, the propeller agitator blade may cause disintegration of the agglomerates formed by the reaction at a higher speed of rotation, whereas such disintegration rarely occurs in practice of the invention.

Having generally described this invention, a more complete understanding can be obtained by reference to certain examples which are provided herein for purposes of illustration only and are not intended to be limiting in any manner.

Figure 2:
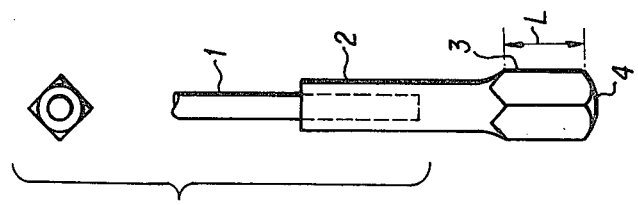
FIGS. 1 and 2 show schematically stirrers A and B, respectively, used in the examples.
Figure 1:
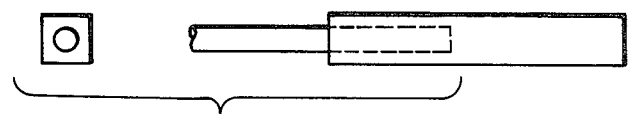

In the examples, the cell used for optical measurement was a transparent plastic cell in a cross-sectional shape of 7 mm square. Two stirrers A and B were used. As shown in FIGS. 1 and 2, stirrer A was composed of a transparent plastic square prism having a cross-section of 4 mm square, the bottom of the prism being flat. The other stirrer B was the same as stirrer A except that the bottom was round and that it comprised two portions, i.e., the lower 6.5 mm long portion in the shape of 4 mm square prism and the upper portion in the shape of a cylinder of 4 mm in diameter. Each stirrer was positioned in the cell such that the longitudinal axis of the stirrer and of the center of the cell were in alignment coaxially and that the distance between the lowermost surface of the stirrer and the bottom of the cell was 2 mm. The light source used was an infrared light emitting device (Monsanto, ME 7124; peak wavelength $0.94\mu$; half-value width of wavelength $0.05\mu$). The light flux having a diameter of 3 mm was penetrated such that its center was positioned at a level of 6 mm above the bottom of the cell. A silicon photo-detector (Bell and Howell, 509-10) was used to detect transmitted light.

EXAMPLE 1

This example illustrates the measurement using an agglutination reaction of an anti-human chorionic gonadotropin (anti-hCG) antibody-sensitized latex.

(1) Preparation of an anti-hCG antibody-sensitized latex

To 10 ml of a solution of anti-hCG antibody in glycine buffer (concentration: 2 mg/ml) was added 1 ml of a polystyrene latex having an average particle diameter of $0.234\mu$ and a solids content of 10% by weight (available from Dow Chemical).

The mixture was stirred for 30 minutes at room temperature, then warmed to 40° C.; stirred for an additional 30 minutes at that temperature and finally centrifuged at 12,000 rpm for 50 minutes under cooling at 2° to 4° C. The precipitates were collected by decantation and the thus separated anti-hCG antibody-sensitized latex particles were suspended in a 0.2 wt. % solution of bovine serum albumin to give an anti-hCG-sensitized latex reagent containing 0.1% by weight sensitized latex particles.

(2) Measurement

Measurement of standard transmittance

To the cell were added 0.2 ml of isotonic saline solution containing 0.2% bovine serum albumin and 0.2 ml of the anti-hCG-sensitized latex reagent as prepared above. The content of the cell was stirred with stirrer A for 3 seconds at 1,400 rpm and subsequently the transmittance ($T_0$) was measured with stirring at 800 rpm. On the basis of the thus obtained value for transmittance To, the change of transmittance of a sample with time resulting from progress of an antigen-antibody reaction was determined in the following way.

Measurement of transmittance

To the cell were added 0.2 ml of a standard hCG solution and 0.2 ml of the anti-hCG-sensitized latex reagent. The content of the cell was stirred with stirrer A for 3 seconds at 1,400 rpm and then the velocity of the stirrer was decreased to 800 rpm. While the stirring was continued at 800 rpm, the measurement of transmittance was made for 8 seconds and then interrupted for 2 seconds and these procedures were repeated. Using the values for average transmittance $T_3$ obtained in the third measurement (i.e., average transmittance between 20 and 28 seconds after the beginning of stirring at 800 rpm) and for average transmittance $T_8$ obtained in the eighth measurement (i.e., average transmittance between 70 and 78 seconds), an average velocity V of change in absorbance was calculated by the following equation:

$V = (60/50) \log (T_3/T_8)$

The results are summarized in Table 1.

TABLE 1

| Concentration of standard hCG solution (IU/ml) | Velocity of change in absorbance (min$^{-1}$) |
| --- | --- |
| 0.111 | 0.0022 |
| | 0.0019 |
| 0.333 | 0.0092 |
| | 0.0082 |
| 1.0 | 0.0243 |
| | 0.0248 |
| 3.0 | 0.0842 |
| | 0.0799 |

As is apparent from Table 1, the results obtained with minute amounts of samples by the method of the invention have good reproducibility since the two measured values for each standard hCG solution given in Table 1 are in good agreement with each other.

EXAMPLE 2

This example illustrates the measurement using an agglutination reaction of an anti-α-fetoprotein (anti-AFP) antibody-sensitized latex.

(1) Preparation of anti-AFP antibody-sensitized latex

An anti-AFP antibody-sensitized latex reagent was prepared in the same manner as described in Example 1 except that the anti-hCG antibody was replaced by anti-AFP antibody and that the final reagent contained 1.0% by weight sensitized latex particles instead of 0.1% by weight in Example 1.

(2) Measurement

Measurement of standard transmittance

The cell was charged with 0.2 ml of isotonic saline solution containing 0.2% bovine serum albumin and 0.05 ml of the anti-AFP antibody-sensitized latex reagent, and 0.25 ml of glycine buffer was added. The transmittance ($T_0$) of the content of the cell was measured with stirring at 1,000 rpm with stirrer A or B.

Measurement of transmittance

To the cell were added 0.2 ml of a standard AFP solution, 0.05 ml of the anti-AFP antibody-sensitized latex reagent and 0.25 ml of glycine buffer. With stirring at 1,000 rpm with stirrer A or B, the transmittance was measured repeatedly for 4 seconds at regular intervals and the values for average transmittance ($T_1$ and $T_2$) between 20 and 24 seconds and between 44 and 48 seconds, respectively, after the beginning of the stirring were determined. From these values the average velocity of change in absorbance, V, was calculated by the following equation:

$V = (60/24) \log (T_1/T_2)$

The results are given in Table 2.

TABLE 2

| Concentration of standard AFP solution (ng/ml) | Velocity of change in absorbance (min$^{-1}$) | | | |
| --- | --- | --- | --- | --- |
| | Stirrer A | | Stirrer B | |
| 100 | 0.0121 | | 0.0115 | |
| | 0.0111 | Average | 0.0104 | Average |
| | 0.0121 | 0.0116 | 0.0135 | 0.0122 |
| | 0.0106 | CV* = 6.1% | 0.0131 | CV = 10.2% |
| | 0.0122 | | 0.0124 | |
| 330 | 0.0310 | | 0.0363 | |
| | 0.0301 | Average | 0.0348 | Average |
| | 0.0320 | 0.0305 | 0.0342 | 0.0350 |
| | 0.0301 | CV = 3.3% | 0.0345 | CV = 2.4% |
| | 0.0293 | | 0.0351 | |
| 1,000 | 0.0976 | | 0.0939 | |
| | 0.1018 | Average | 0.0941 | Average |
| | 0.0886 | 0.0961 | 0.0986 | 0.0940 |
| | 0.0972 | CV = 5.0% | 0.0985 | CV = 5.9% |
| | 0.0954 | | 0.0849 | |
| 3,000 | 0.2811 | | 0.2364 | |
| | 0.2699 | Average | 0.2519 | Average |
| | 0.2717 | 0.2646 | 0.2766 | 0.2413 |
| | 0.2785 | CV = 9.6% | 0.2245 | CV = 9.8% |
| | 0.2197 | | 0.2172 | |

*CV: Coefficient of variation

EXAMPLE 3

Effect of volume of liquid in cell

The cell was charged with 0.1 ml of isotonic saline solution containing bovine serum albumin and 0.05 ml of the anti-AFP antibody-sensitized latex reagent prepared in Example 2, and 0.25 ml of glycine buffer was added. While the content of the cell was stirred at 1,000 rpm with stirrer A or B, the variation of transmittance with time was measured. When stirrer B was used, only little variation of transmittance with time was found. In contrast with this, when stirrer A was used, it was found that the transmittance might be varied irregularly due to entrapment of air bubbles, thereby the measurement being significantly hindered. Typical charts of transmittance obtained with stirrers A and B are shown in FIGS. 3 and 4, respectively.

From comparison between Examples 2 and 3, it can be seen that stirrer B is superior when a relatively small volume of liquid is contained in the cell.

From comparison between Examples 1 and 3, it can be seen that stirrer B is superior also in the case where the stirrer is rotated at a high velocity. It is believed that these results are due to the fact that stirrer A has a larger tendency to cause entrapment of air bubbles as it is rotated.

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A method for optically assaying a liquid sample which comprises placing the liquid sample in a cell for optical measurement equipped with a stirrer having a thick polygonal prism portion made of a transparent material, said polygonal prism portion of the stirrer being positioned within the path of light used for the measurement, and measuring an optical property of the sample with stirring by rotation of the stirrer.

2. The method for optical assay according to claim 1 wherein the portion of the stirrer located in the neighborhood of the liquid surface is in the shape of a cylinder.

3. The method for optical assay according to claim 2 wherein said cylindrical portion of the stirrer extends to a depth of at least 1 mm below the liquid surface.

4. The method for optical assay according to claim 2 wherein said cylindrical portion of the stirrer extends to a depth of 1 to 5 mm below the liquid surface.

5. The method for optical assay according to claim 1, 2, 3 or 4 wherein the polygonal prism portion of the stirrer has a length equivalent to at least 30% of the depth of the liquid in the cell when the stirrer is inserted into the liquid.

6. The method for optical assay according to claim 1, 2, 3 or 4 wherein the minimum distance between the stirrer and the inner wall of the cell is in the range of 0.5 to 2.0 mm when the stirrer is rotated.

7. The method for optical assay according to claim 1, 2, 3 or 4 wherein the cross-sectional area of the polygonal prism portion of the stirrer occupies at least 25% of the effective cross-sectional area of the portion of the cell in which the polygonal prism portion of the stirrer is located.

8. The method for optical assay according to claim 1, 2, 3 or 4 wherein the polygonal prism portion of the stirrer is rectangular in cross-section.

9. The method for optical assay according to claim 1, 2, 3 or 4 wherein the polygonal prism portion of the stirrer is square in cross-section.

10. The method for optical assay according to claim 1, 2, 3 or 4 wherein the cross-section of the cell is rectangular.

11. The method for optical assay according to claim 1, 2, 3 or 4 wherein the cross-section of the cell is square.

12. The method for optical assay according to claim 1, 2, 3 or 4 wherein the liquid sample comprises inert carrier particles sensitized with an antigen or antibody, together with the appropriate antibody or antigen.

13. The method for optical assay according to claim 1, 2, 3 or 4 wherein the liquid sample is measured for light transmittance therethrough.

* * * * *